United States Patent [19]

Adams

[11] Patent Number: 5,488,961

[45] Date of Patent: Feb. 6, 1996

[54] HYDROPHOBIC EAR PLUGS

[76] Inventor: Daniel O. Adams, 1145 Tonkawa Rd. South, Orono, Minn. 55356

[21] Appl. No.: 346,741

[22] Filed: Nov. 30, 1994

[51] Int. Cl.$^6$ .............................. A61F 11/00; A61F 11/06
[52] U.S. Cl. ............................................. 128/864; 128/867
[58] Field of Search ..................... 128/846, 864, 128/865, 866, 858, 859, 867, 868; 2/2, 209; 181/129

[56] References Cited

U.S. PATENT DOCUMENTS

| | | | |
|---|---|---|---|
| 706,975 | 8/1902 | Macbeth | 128/864 |
| 904,715 | 11/1908 | McWilliams | 128/864 |
| 1,279,396 | 9/1918 | Wilson | 128/868 |
| 1,355,276 | 10/1920 | Schultz | 128/864 |
| 2,070,403 | 2/1937 | Hershman | 128/864 |
| 3,842,829 | 10/1974 | Ellis | 128/868 |
| 4,465,159 | 8/1984 | Stallings | 181/129 |
| 4,537,187 | 8/1985 | Scott | 128/151 |
| 4,540,063 | 9/1985 | Ochi et al. | 181/135 |
| 4,683,587 | 7/1987 | Silverman | 381/25 |
| 5,113,967 | 5/1992 | Killion et al. | 181/132 |

OTHER PUBLICATIONS

*Versapor®R Membrane–hydrophobic for venting applications, GelmanSciences Membrane & Device Division Product Data*, Sep. 1993.
Doc's Proplugs® *Performed Protective Earplugs*, Nov. 1993.

*Primary Examiner*—Michael A. Brown
*Attorney, Agent, or Firm*—Nawrocki, Rooney & Sivertson

[57] ABSTRACT

Ear plugs for swimming, snorkeling, scuba diving and other water related activities form a watertight seal within an individual's outer ear canals. The ear plugs have a lumen extending along the ear canal. A hydrophobic membrane extending across the lumen, which admits air into or out of the ear canal but blocks water, seals the ear against water but transmits air. This passage of air equalizes pressure across the plug, improves hearing with the ear plug in place, and prevents water contaminants, such as harmful infectious agents and pollutants, from entering the ear canal.

13 Claims, 8 Drawing Sheets

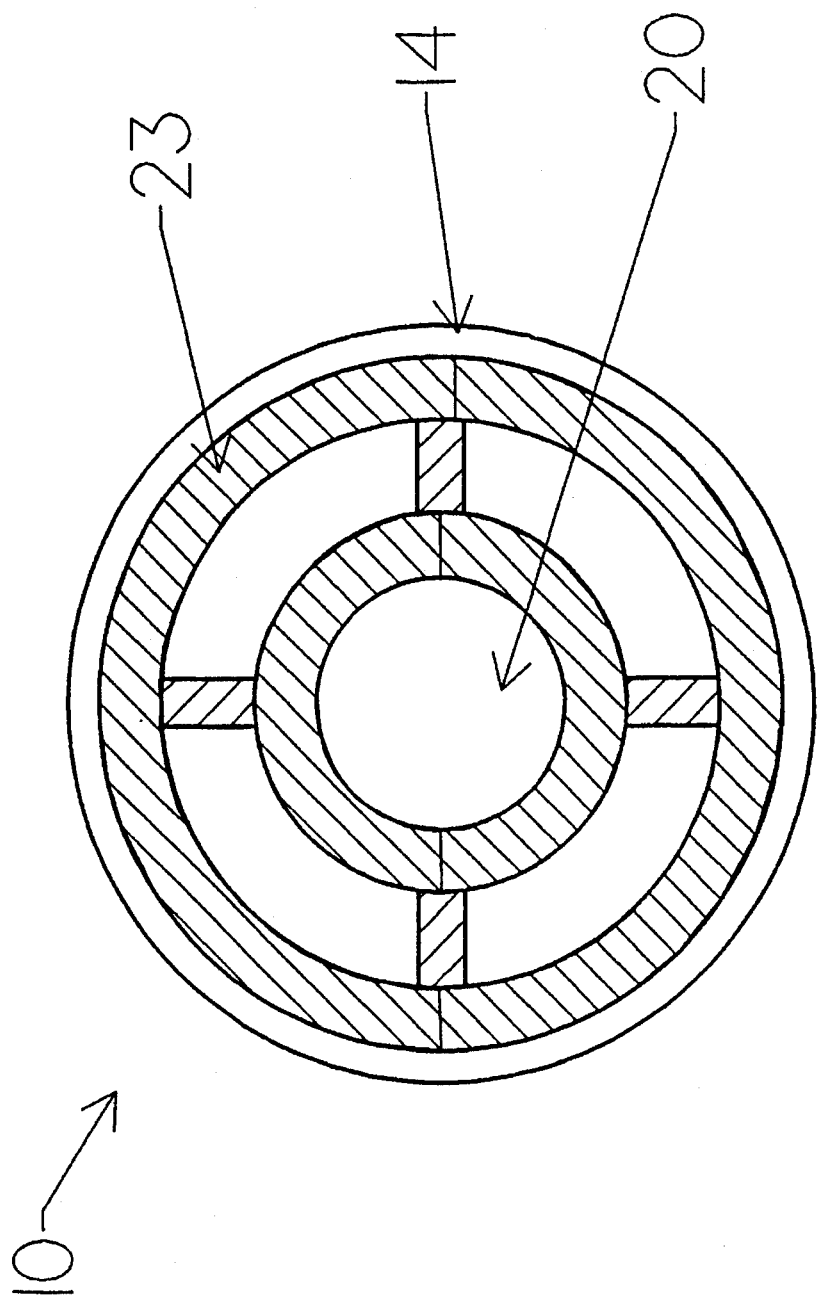

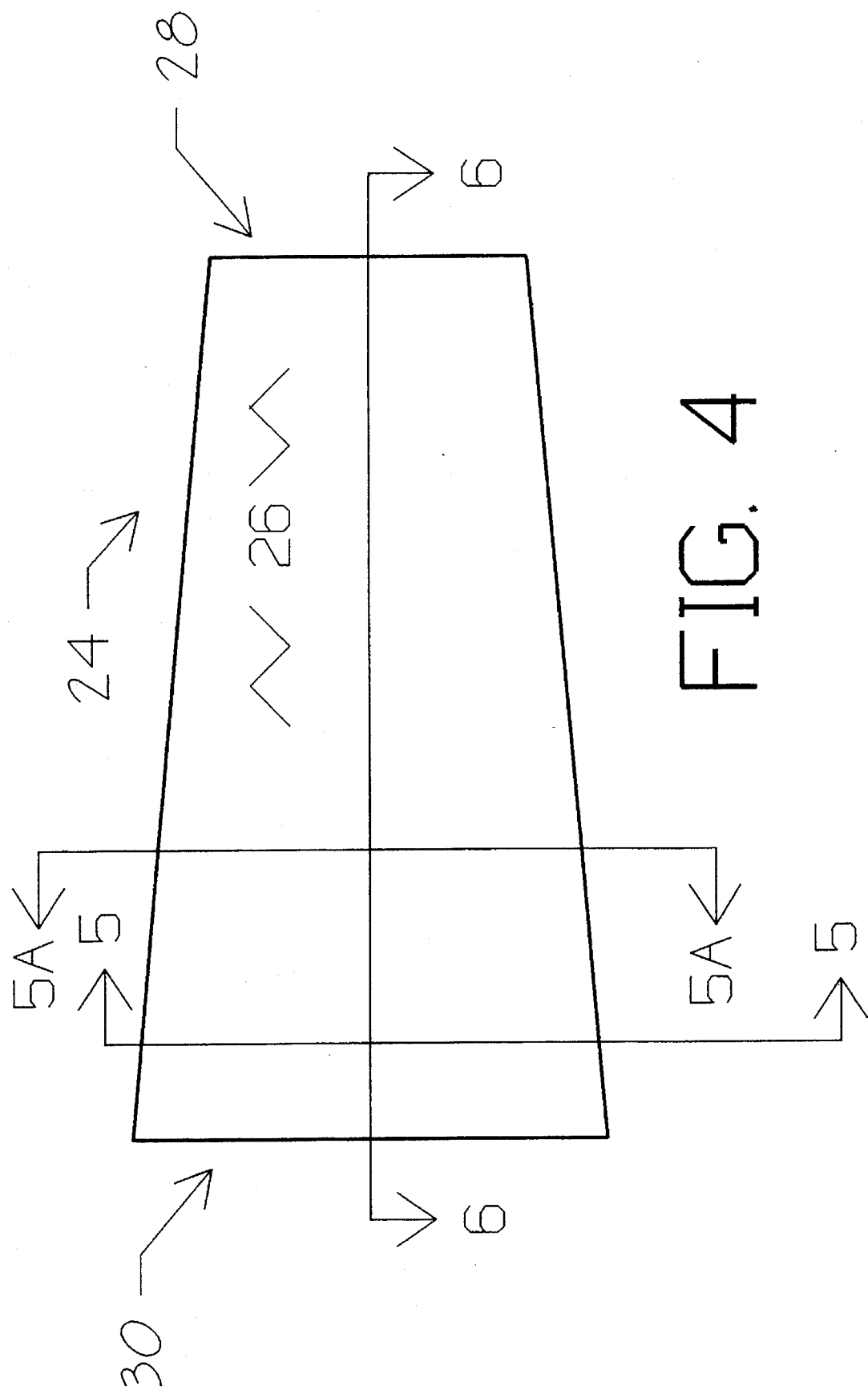

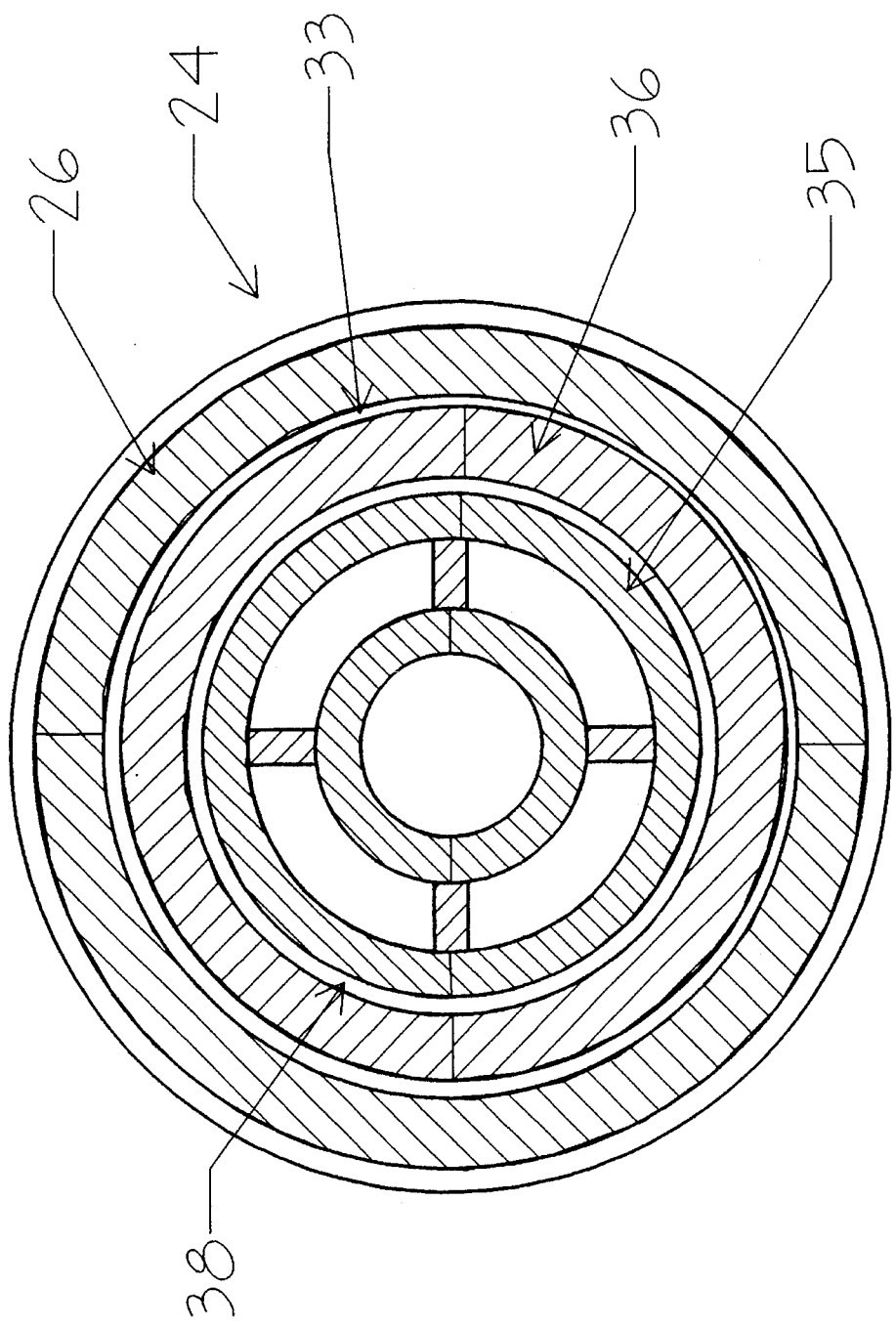

HYDROPHOBIC EAR PLUGS

FIELD OF THE INVENTION

The present invention relates to ear plugs which blocks water from entering the ear canal but which transmits air into or out of the ear canal.

BACKGROUND OF THE INVENTION

Many people who enjoy water related activities have the problem that water entering the ear canal may not drain away for hours or even days. This can also result in a pressure differential between the inner and outer ear with resulting pain and hearing problems both during the water activity and later. The exposure of the delicate tissues of the ear to untreated water, which may contain harmful substances and infectious agents, can cause ear infections or other negative reactions.

A number of ear plugs used for a variety of different purposes are available. In Carrigan, U.S. Pat. No. 5,332,871, an earplug having a hole therethrough closed by a manually operated valve allows the user to open the valve for improved hearing without removing the plug. In Ochi et al. U.S. Pat. No. 4,540,063, an ear plug which attenuates sound waves of particular frequencies is described. Neither of these are intended to be used in the water.

A number of other available plugs are designed for protection against water entering the ear canal and to protect the ear against loud noises. In general, these use a design that simply seals off the ear canal by a variety of sealing means.

None of these ear plugs provide a watertight seal of the ear canal along with means for admitting or discharging air to minimize or prevent differential pressure across the plug, to improve hearing underwater and to allow hearing while the ear plug is sealed within the ear whether underwater or not.

SUMMARY OF THE INVENTION

An ear plug, having a lumen through the plug along the ear canal, provides a watertight seal of the ear canal but admits air into the canal by means of a membrane made of hydrophobic material extending across the lumen. Hydrophobic material contains pores which are arranged and sized to transmit air but which block water up to a given water pressure. The quantity of air passed through the material is a direct function of pore size and of membrane area. Water break-through pressure, which is the pressure where water is no longer blocked by the hydrophobic material, is an inverse function of pore size. The selected pore size is larger for use near the surface of the water for swimming and snorkeling than for scuba diving at greater depths. At greater depths the membrane may need to be supported by a grille structure on the inner side to withstand the higher water pressure. Separate membranes can also be stacked to provide a greater water pressure resistance.

In a first embodiment, where only one maximum depth use is contemplated, the hydrophobic membrane is permanently attached across the lumen. In a second embodiment, where a range of maximum depth use is contemplated, one or more hydrophobic membranes are mounted within a membrane mounting assembly. The membrane mounting assembly mates with the lumen to permit exchanging membranes easily. This permits using a single pair of ear plugs for a number of water depths.

BRIEF DESCRIPTION OF THE DRAWINGS

The objects and many of the attendant advantages of the present invention will be readily appreciated as it becomes better understood in connection with the accompanying drawings, in which like reference numerals designate like parts throughout the figures thereof and wherein:

FIG. 3A is a cross-section taken along 3A—3A of FIG. 1.

FIG. 4 is a side view of a second embodiment of the invention.

FIG. 5A is a cross-section taken along 5A—5A of FIG. 4.

PREFERRED EMBODIMENTS

Figure 1:
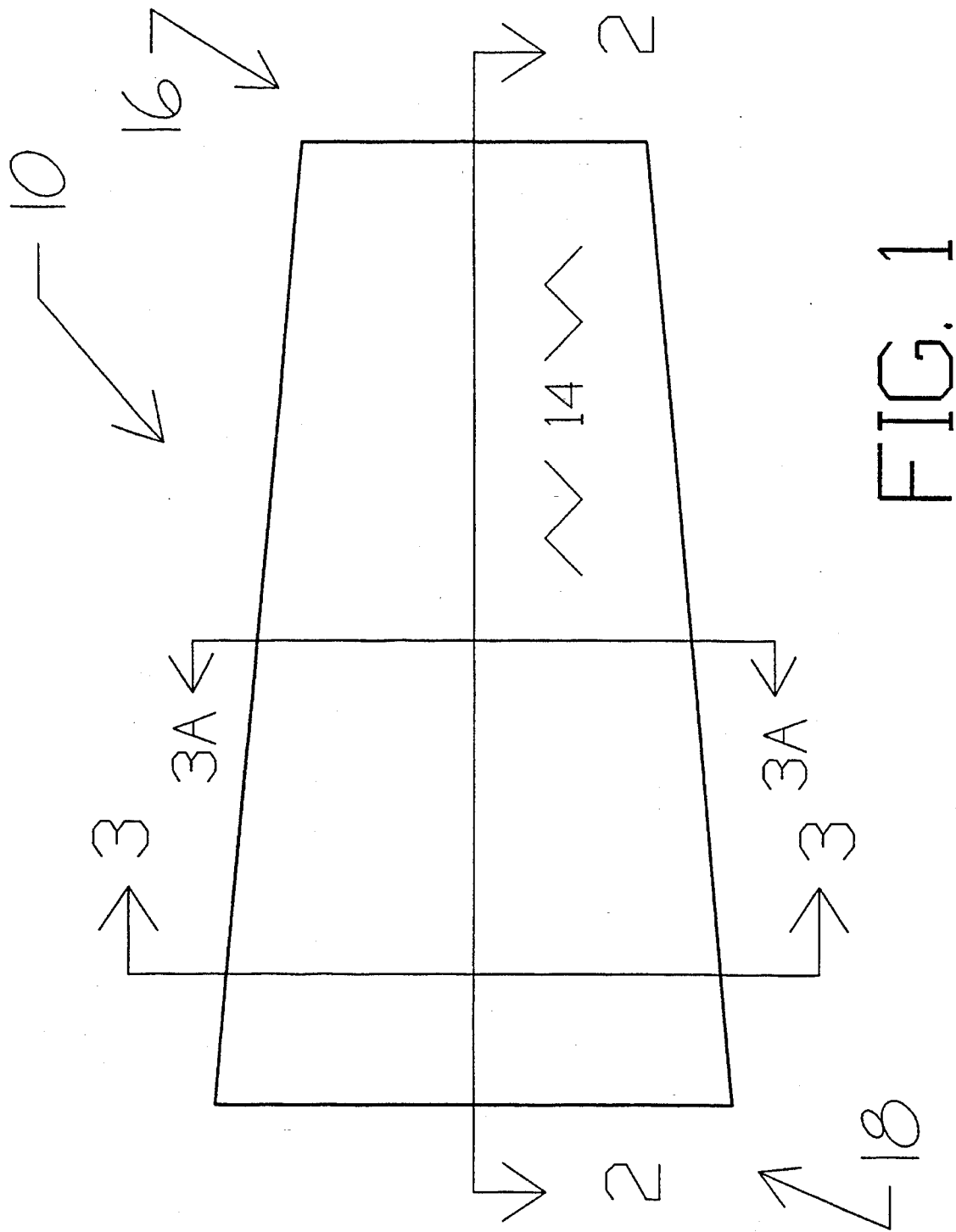
FIG. 1 is a side view of a first embodiment of the invention.

A first embodiment of the invention has a membrane of hydrophobic material permanently attached across a lumen through the plug for use at or near a single water depth.

In FIGS. 1–3A the first embodiment of the invention is shown. Ear plug 10 has a body 14 with a distal end 16 inserted within an ear canal closest to the ear drum and a proximal end 18 at the opposite outer end. Body 14 is generally wedge shaped to fit the ear canal and provide a tapered watertight seal.

Membrane 22 of hydrophobic material has an optional support structure 23 mounted against its inner side. Support structure 23 is not required for shallow water depth use but may be required for use at greater depths. Support structure 23 is in the shape of two concentric circles joined together by four radial extensions. This provides a great deal of supporting strength against water pressure.

Figure 2:
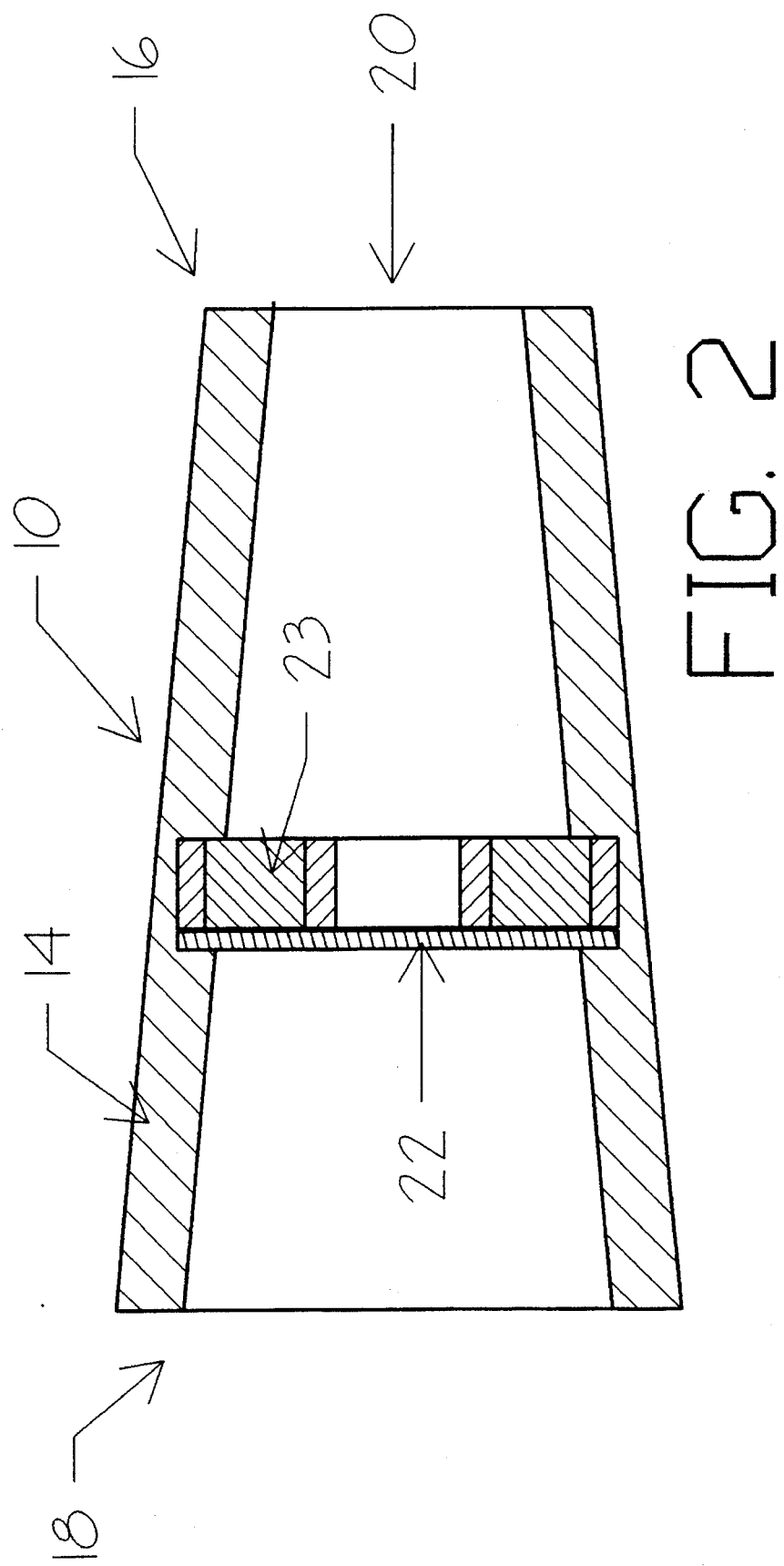
FIG. 2 is a cross-section taken along 2—2 of FIG. 1.
Figure 3:
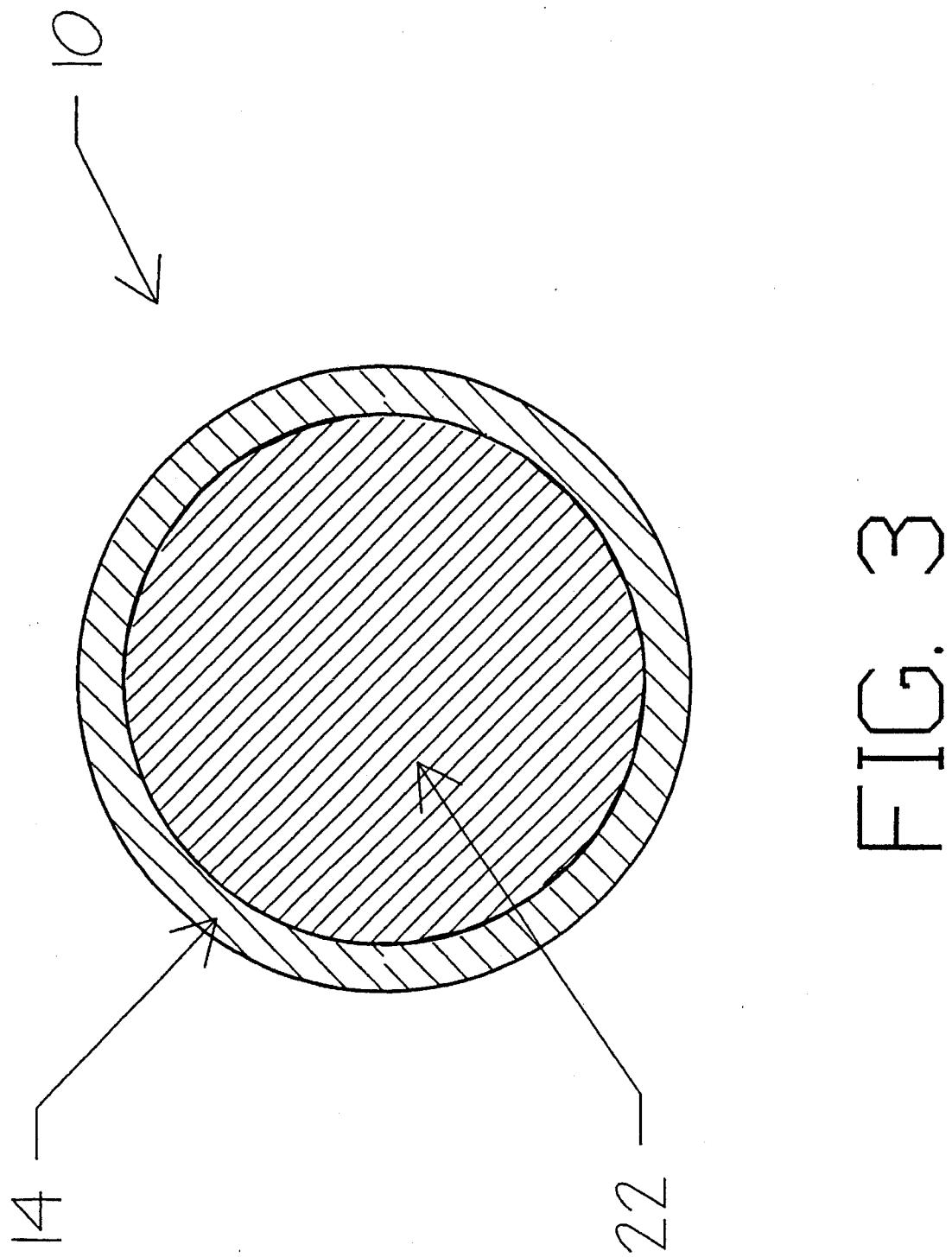
FIG. 3 is a cross-section taken along 3—3 of FIG. 1.

In FIG. 2, lumen 20, extending completely through body 14 from distal end 16 to proximal end 18, membrane 22 extending completely across lumen 20, and supporting structure 23 adjacent to the inner surface of the membrane, are shown. Membrane 22 and supporting structure 23 extend into the walls of body 14 to form a watertight seal between body 14 and these parts. In FIG. 3, membrane 22 is also shown extending completely across lumen 20. In FIG. 3A the concentric rings and interconnecting radials of support frame 23 are shown.

Those skilled in the art will recognize that a number of alternative means and shapes to provide a seal between an ear plug and ear canal can be employed. As an example, a set of parallel flexible extensions around the surface of body 14 perpendicular to ear canal 12 can be employed as an alternative sealing means. Body 14 can also be made from a cast taken of the ear canal itself for an exact fit.

A flexible member can also be attached to and extend from the proximal end 18 of body 14 outward to assist in removing the plug from the ear canal.

Methods of manufacturing ear plugs are well known in the art and include such means as insert injection molding techniques, resin casting and centrifugal molding. A number of polymers are suitable for the material of ear plugs including such representative materials as: polyethylene, polypropylene, silicone, PVC and nylon.

Hydrophobic material will transmit air in either direction depending upon the driving differential pressure across the material but will block water below a given water pressure.

The preferred material for membrane 22 is a modified white acrylic copolymer, available from Gelman Sciences Membrane & Device Division of Ann Arbor, Mich. under the registered trade name of "Versapor R" Membrane. This membrane is currently manufactured with a thickness of 2.5 to 5 mils. and with pore sizes from 0.2 micron to 10 microns.

Membranes with a 0.2 micron pore size have a water break-through rating of 26 lbs. per sq. in. pressure and an air flow rate of 4.5 liters per minute per 3.7 sq. cm. of membrane area under a differential driving pressure across the membrane of 13.5 lbs. per square in., while a membrane with a 3 micron pore size has a water break-through rating of 3 lbs. per sq. in. pressure and an air flow rate of 55 liters per minute per 3.7 sq. cm. of membrane area under a differential driving pressure across the membrane of 5.0 lbs. per square in. By changing the membrane surface area and pore size a desired balance between the desired degree of protection against water infiltration into the ear drum, represented by the water break-through rating, and the necessary air infiltration, to relieve pressure differential across the plug to allow for improved hearing, can be obtained.

The Versapor V-3000R membrane has a water break-through rating of 3 psi which would allow swimming to a depth of between 6 and 7 feet. The high air flow rates of this membrane would allow acceptable hearing above the water surface without the need to remove the ear plug from the ear and relieve any pressure differential across the plug. This helps insure that the ear plug is not forced from the ear canal by differential pressure. A generally circular shaped membrane area with approximately 0.2 inch diameter, which fits into the cross-section of an ear plug, will provide acceptable characteristics for this use.

If greater depth use is desired a smaller pore size membrane may be used or two or more membranes can be stacked to obtain the desired water break-through pressure. As mentioned earlier, a support structure backing up the membrane may also be required at great water depths. The Versapor R V-200R membrane has a water break-through pressure of 26 psi, which would permit use at approximately 60 ft. of water depth. These trade-offs of pore size and membrane area permits selecting desired water break-through rates and air infiltration rates for improved hearing and reduced differential pressure rates for a wide range of depths.

Membranes of acceptable hydrophobic material are also available from Performance Systematic Inc. of Caledonia, Mich. These filters are made of T.F.E. coated micro glass and are available in a variety of thickness and pore sizes similar to those described above in their TA product series. This series packages the hydrophobic membranes within a cartridge shaped mounting means to provide a means of rapid membrane replacement.

Any hydrophobic material, which blocks water up to an acceptable water pressure but which transmits an acceptable quantity of air in either direction through the material, is suitable for this application. It is anticipated that a number of additional materials having these necessary characteristics will become available in the future. The above remarks also apply to the following second embodiment description.

Figure 5:
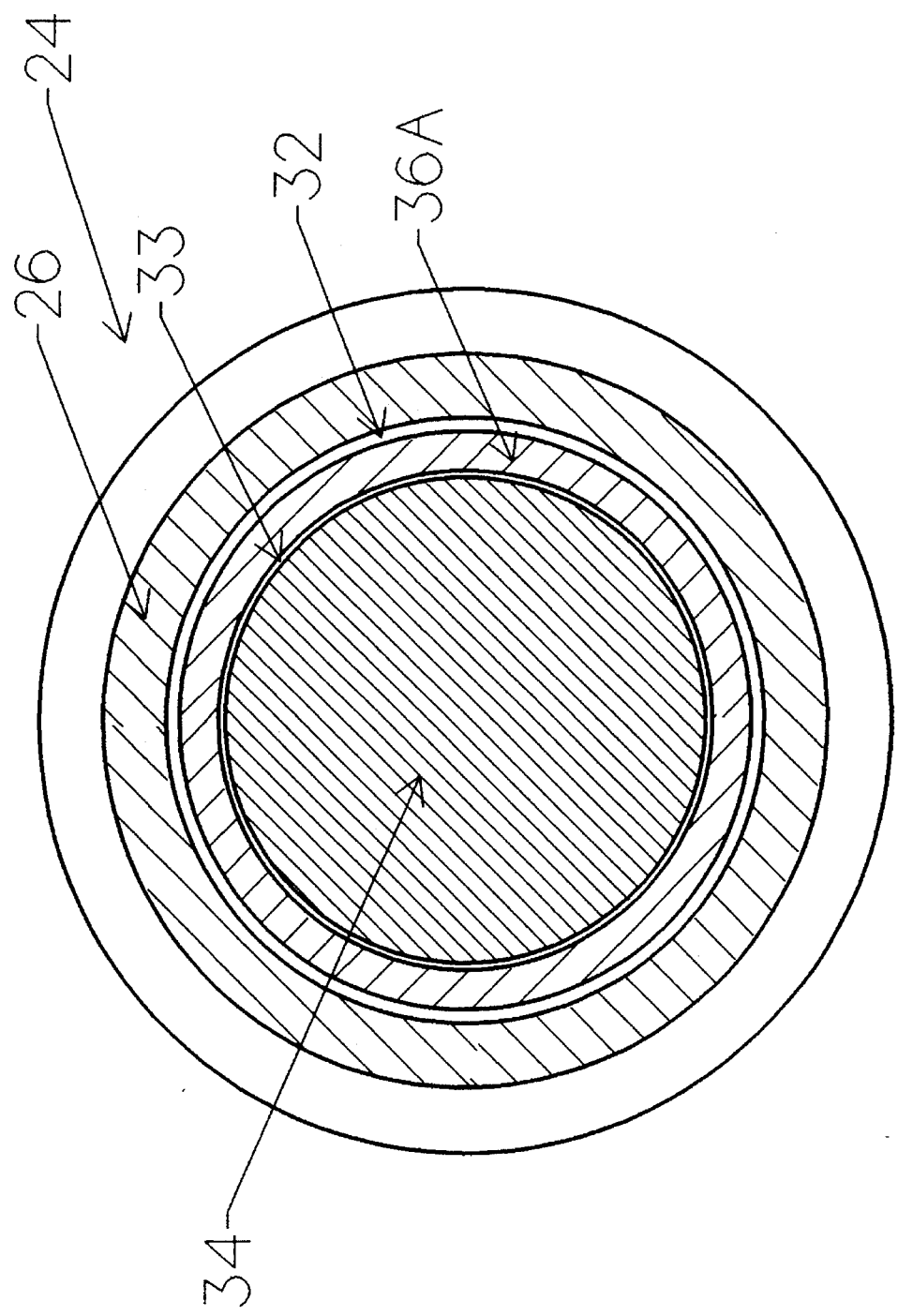
FIG. 5 is a cross-section taken along 5—5 of FIG. 4.
Figure 6:
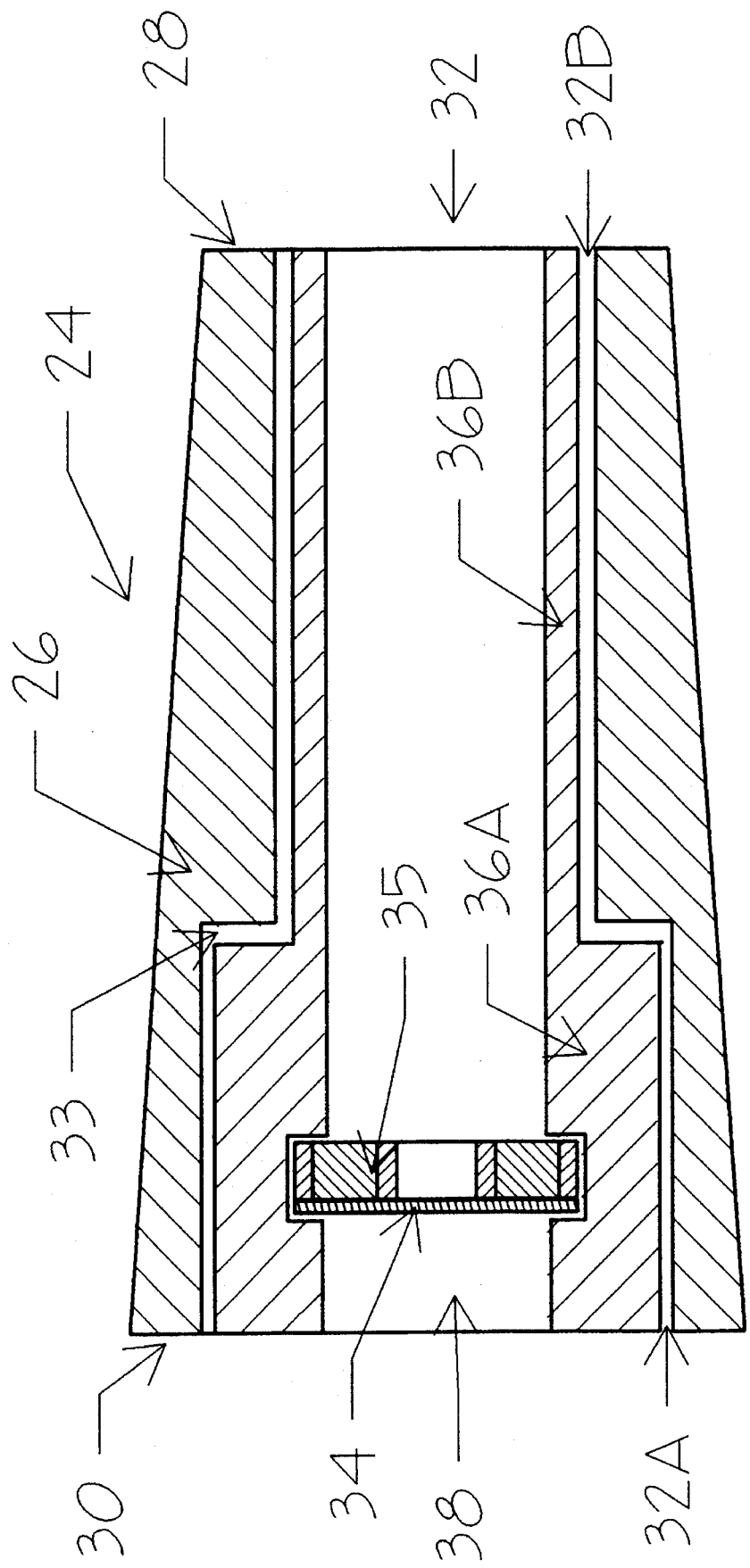
FIG. 6 is a cross-section taken along 6—6 of FIG. 4.

In FIGS. 4–6, a second embodiment is shown, which provides a means of readily replacing hydrophobic membranes to permit use of a single pair of ear plugs at a number of maximum water depths. In FIG. 4, ear plug 24 has a body 26 with a distal end 28 which is placed in the ear canal closest to the ear drum of the user, and a proximal end 30 which is located at the outer end of the ear canal.

Note that while body 10 in FIGS. 1–3 and body 26 in FIGS. 3–6 are depicted as having a circular cross-section this is a simplification in that an actual ear canal is essentially elliptical in cross-section. The critical parameter here is providing a watertight seal with the ear canal. As discussed earlier, a variety of shapes including a cast of the ear canal which is known to those skilled in the art, can be used to provide such a seal. Here body 26 is also generally wedge shaped to fit the ear canal and provide a tapered watertight seal.

In FIGS. 5, 5A and 6 lumen 32, extending completely through body 26 from distal end 28 to proximal end 30, is shown. Lumen 32 is comprised of two portions, proximal portion 32A and distal portion 32B. The proximal portion 32A of lumen is enlarged to form a bore 33, the purpose of which will be discussed later.

Hydrophobic membrane 34 has a support frame 35, both being sealingly mounted within mounting assembly 36 with the support frame on the inner side of the ear canal, to assist the membrane in withstanding outside water pressure. Mounting assembly 36 provides the mounting means for both membrane 34 and support frame 35. Mounting assembly 36 is generally cylindrical in shape having the proximal portion 36A stepping down to a smaller diameter distal portion 36B. The side walls of both of these portions are essentially the same thickness resulting in the circular cross-section area of proximal portion being larger than the circular cross-section of the distal portion to match the surface of lumen 32. Membrane 34 and support frame 35 are sealingly mounted across mounting assembly 36, which extends through lumen 32 in body 26. The outer surface of mounting assembly 36 sealingly mates with the interior of lumen 32 along its full length.

The spacings shown between the parts in FIG. 5, 5A and 6 are exaggerated to permit distinguishing the various parts. In the actual assembly membrane 34 and support frame 35 would be welded or sealingly affixed across lumen 38 in mounting assembly 36. The outer surfaces of mounting assembly 36 would fit sealingly within the surfaces of lumen 32. Further, the distal portion of lumen 32 tapers slightly inward from the set-back toward the distal end to provide a wedging watertight seal with the opposed surface of mounting assembly 36. Since the water pressure is always applied to the proximal end of ear plug 24, this wedging effect will also secure mounting assembly 36 securely in place. While mounting assembly 36 is shown holding one membrane, the mounting assembly can hold two or more membranes, if required.

With ear plug 24 removed from the ear canal, mounting assembly 36 can readily be removed from body 26 by inserting a blunt object into lumen 32 from distal end 28 and pressing against the membrane or support frame. After removal, a different mounting assembly 36 holding a membrane or membranes with different parameters can be reinserted into the proximal end Of body 26 for use at a different maximum depth.

The use of an ear plug, which incorporates hydrophobic material in the form of a membrane to permit the passage of air while blocking the passage of water, overcomes a long-standing problem of water sportsmen. As described earlier, the blockage of water eliminates the problem of delayed water drainage and exposure to water contaminants, while permitting the passage of air will minimize or eliminate the problem of differential water pressure across the ear plug. Contaminants are a constantly increasing problem because of increased environmental pollution. Allowing air passage through the membrane provides improved hearing and reduces discomfort. Improved hearing without removing the ear plugs is a great convenience as well as a safety feature.

While this invention has been described with respect to two specific embodiments, those skilled in the arm will recognize that a number of variations can be made which are within the range of this invention. Accordingly, the scope of the coverage are those described in the following claims.

I claim:

1. An ear plug comprising:
   a) a body having a proximal end and a distal end, being sized and shaped to sealingly fit within an ear canal with the proximal end at the outer end of the ear canal and the distal end within the ear canal at the opposite end therefrom, said body further having a lumen extending from the proximal end to the distal end such as to extend within and through the ear canal when the body is mounted therein; and
   b) means for preventing the transmission of water and permitting the transmission of air, said means being attached to said body within, extending across and sealing said lumen.

2. An ear plug as in claim 1 wherein said means for preventing the transmission of water and permitting the transmission of air comprises at least one hydrophobic membrane.

3. An ear plug as in claim 2 further having a support structure for said membrane extending across said lumen adjacent to the side of said membrane closest to the distal end of said body.

4. An ear plug as in claim 2 with said membrane having pores with a minimum size of 0.2 microns and a maximum size of 10 microns.

5. An ear plug as in claim 2 with said membrane having a water break through rating of not less than 3 pounds per square inch.

6. An ear plug as in claim 2 with said membrane having an air flow rate therethrough of not less than 4.5 liters of air per 3.7 square centimeters of membrane area.

7. An ear plug as in claim 1 having replacement means for replacing with another said means for preventing the transmission of water and permitting the transmission of air.

8. An ear plug as in claim 7, wherein said means for preventing the transmission of water and permitting the transmission of air comprises at least one hydrophobic membrane, and wherein said means for replacing with another said means for preventing the transmission of water and permitting the transmission of air comprises a replaceable membrane mounting means for sealingly securing said membrane across said lumen.

9. An ear plug as in claim 8 further having a support structure for said membrane extending across said lumen adjacent to the side of said membrane closest to the distal end of said body.

10. An ear plug as in claim 8 with said membrane having pores with a minimum size of 0.2 microns and a maximum size of 10 microns.

11. An ear plug as in claim 8 with said membrane having a water break through rating of not less than 3 pounds per square inch.

12. An ear plug as in claim 8 with said membrane having an air flow rate therethrough of not less than 4.5 liters of air per 3.7 square centimeters of membrane area.

13. An ear plug as in claim 8 wherein said membrane mounting means comprises a mounting assembly sized to sealingly fit within said lumen through said body, said mounting assembly having a proximal end and a distal end which are adjacent to the respective proximal and distal end of said body when fit within said lumen, said mounting assembly further having a lumen therethrough extending from the proximal to the distal end with at least one membrane extending sealingly across.

* * * * *